United States Patent
Felton et al.

(10) Patent No.: US 11,497,607 B2
(45) Date of Patent: Nov. 15, 2022

(54) PENILE IMPLANT FOR NEOPHALLUS

(71) Applicant: Boston Scientific Scimed, Inc., Maple Grove, MN (US)

(72) Inventors: Jessica Elizabeth Felton, Minneapolis, MN (US); Thomas Andrew Albrecht, Edina, MN (US); Matthew Lee Nelson, Plymouth, MN (US); Brian P. Watschke, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 44 days.

(21) Appl. No.: 16/946,210

(22) Filed: Jun. 10, 2020

(65) Prior Publication Data

US 2020/0397584 A1  Dec. 24, 2020

Related U.S. Application Data

(60) Provisional application No. 62/864,003, filed on Jun. 20, 2019.

(51) Int. Cl.
*A61F 2/26* (2006.01)

(52) U.S. Cl.
CPC ............ *A61F 2/26* (2013.01); *A61F 2210/00* (2013.01); *A61F 2220/0008* (2013.01); *A61F 2230/006* (2013.01); *A61F 2250/0003* (2013.01)

(58) Field of Classification Search
CPC ........................................................ A61F 2/26
See application file for complete search history.

(56) References Cited

U.S. PATENT DOCUMENTS

| 4,335,714 | A | 6/1982 | Edgerton et al. |
| 10,722,367 | B2 * | 7/2020 | Kansas ................... A61L 27/16 |
| 2018/0098854 | A1 | 4/2018 | Allen et al. |

FOREIGN PATENT DOCUMENTS

| WO | 2017009580 A1 | 1/2017 |
| WO | 2020092718 A1 | 5/2020 |

OTHER PUBLICATIONS

Invitation to Pay Additional Fees and Partial International Search for PCT Application No. PCT/US2020/070141, dated Sep. 22, 2020, 10 pages.

* cited by examiner

*Primary Examiner* — John P Lacyk
(74) *Attorney, Agent, or Firm* — Brake Hughes Bellermann LLP

(57) ABSTRACT

According to an aspect, an implantable device for penile construction includes a penile implant having a distal portion and a proximal portion. The distal portion includes a shaft portion configured to be disposed in a neophallus. The proximal portion defines a first strut and a second strut, and the proximal portion is configured to be attached to a pelvis structure.

14 Claims, 10 Drawing Sheets

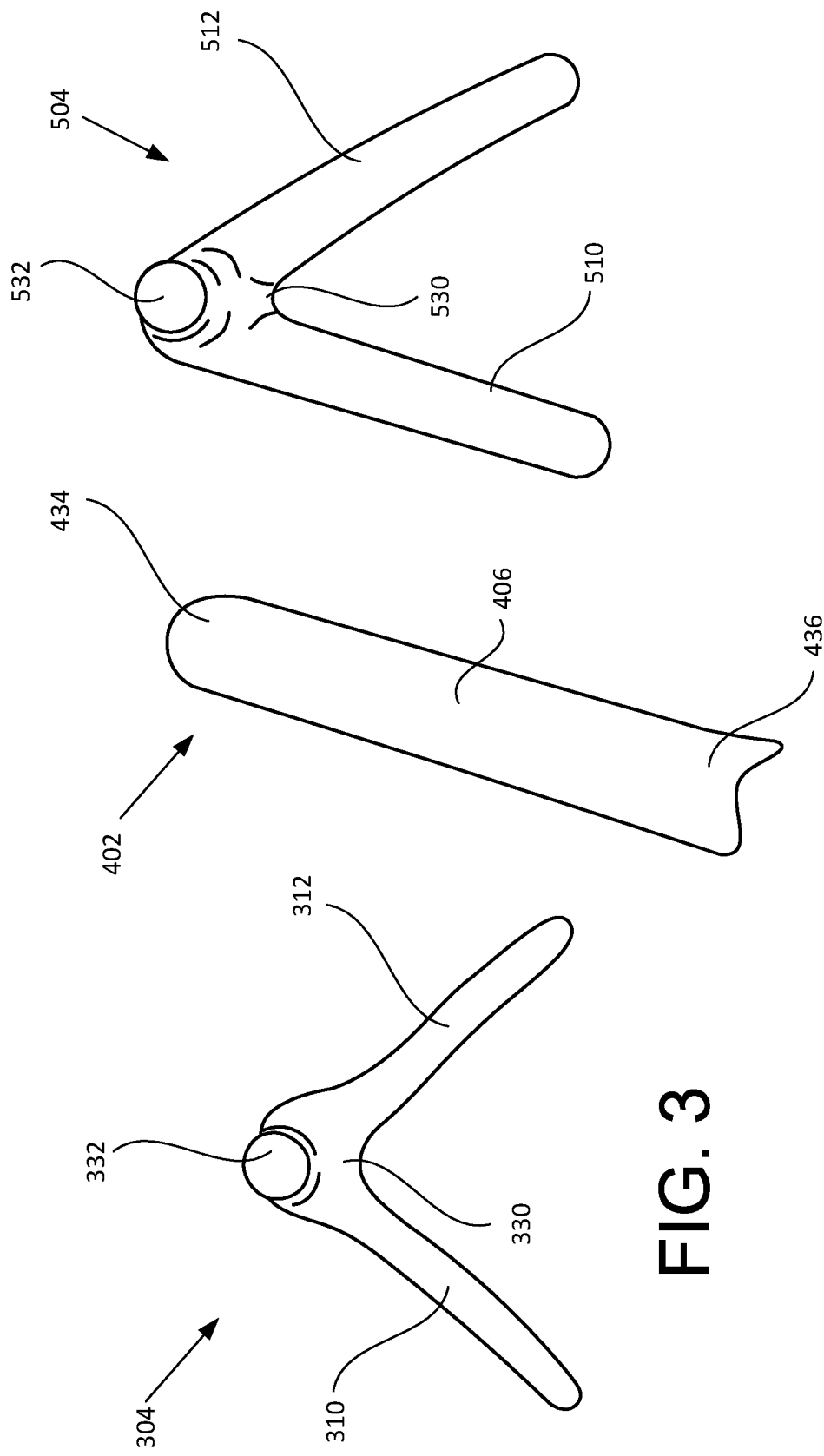

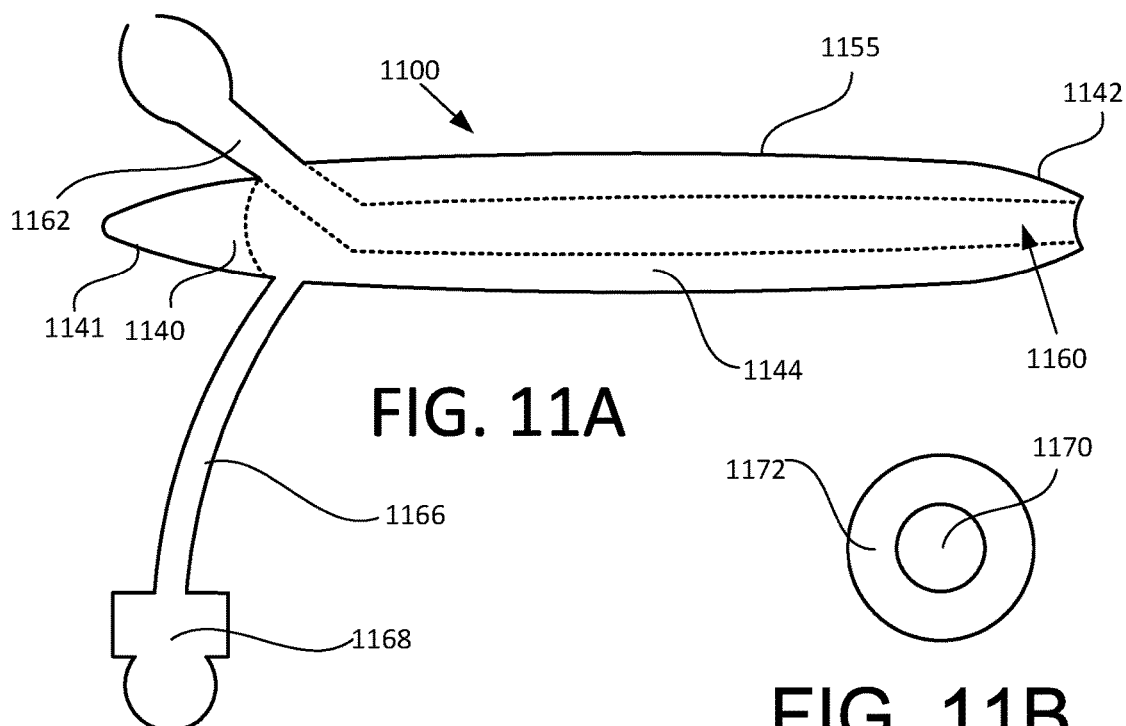
FIG. 11A
FIG. 11B
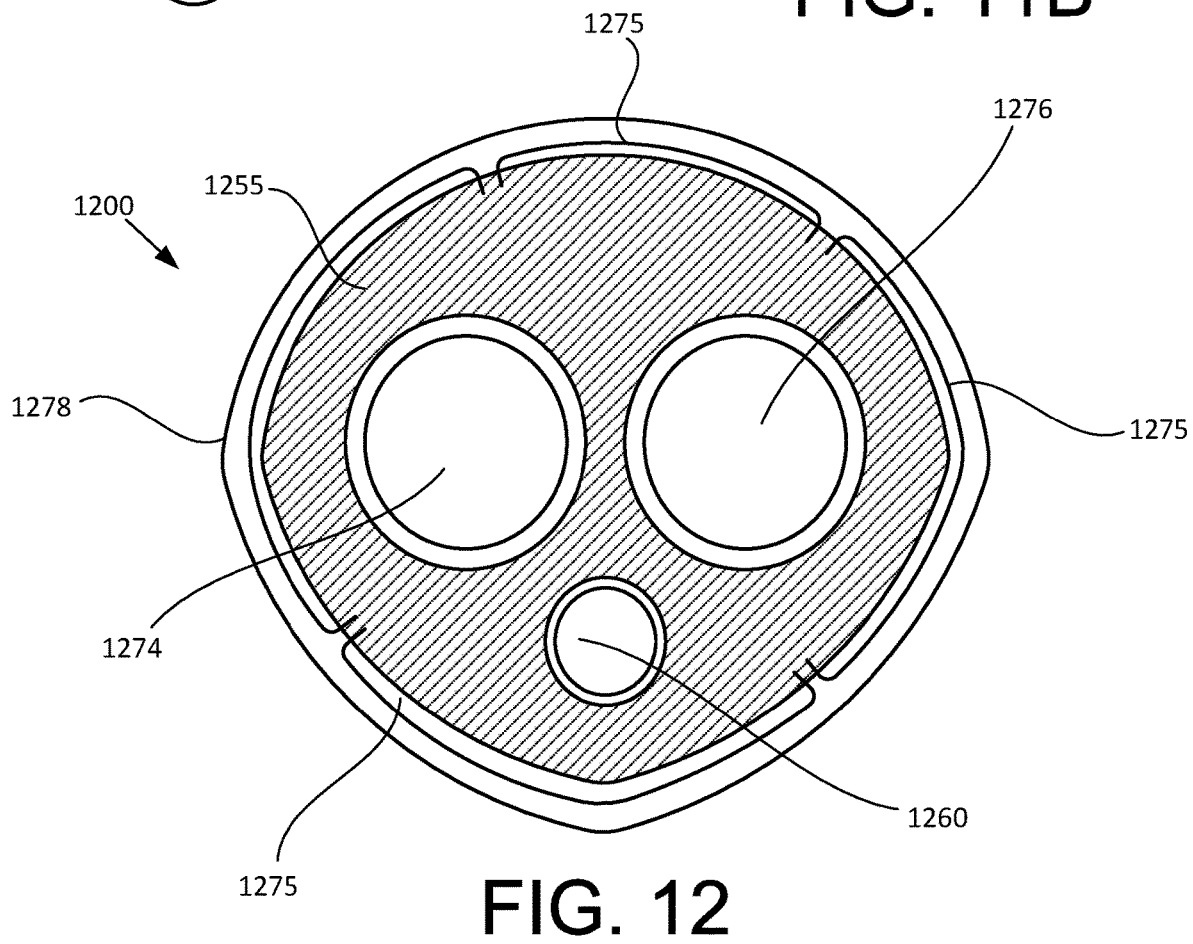
FIG. 12

PENILE IMPLANT FOR NEOPHALLUS

CROSS-REFERENCE TO RELATED APPLICATION

This application claims priority to U.S. Patent Application No. 62/864,003, filed on Jun. 20, 2019, entitled "PENILE IMPLANT FOR NEOPHALLUS", which is incorporated by reference herein in its entirety.

TECHNICAL FIELD

This disclosure relates generally to penile implants for a neophallus.

BACKGROUND

In some examples, penile prostheses for erectile dysfunction have been used off-label in penile construction or reconstruction cases such as female to male transgender, and natal males with penile reconstruction (e.g., congenital disorders, amputation (penile cancer), trauma, etc.). For example, a patient undergoes a phalloplasty procedure (e.g., single stage or multiple stages) in which a neophallus is surgically constructed from tissue grafts taken from other parts of the body. The phalloplasty procedure may be considered highly invasive with relatively high infection risks, and a patient may be open on the operating table for an extended period of time (e.g., 8+ hours). Since the neophallus is made of skin and does not contain the erectile tissues of a biological penis, the neophallus does not have the capability to achieve an erection.

A penile prosthesis may be implanted after the phalloplasty procedure. In some examples, the penile prosthesis may be a transgender specific device or a penile prosthesis used for erectile dysfunction in natal males. However, there may be difficulties associated with how the penile prosthesis is attached to the pelvic. In natal males, the proximal ends of the corpora cavernosa tunnel deep into the pelvis, and, in some examples, they provide the cavity in which the two cylinders of the penile prosthesis are disposed, as well as a way to prevent migration or crossover of the cylinders. In the natal males undergoing penile reconstruction due to amputation (as well as other situations), the proximal corpora may still be intact and may serve to anchor the proximal ends of the penile prosthesis dual cylinders. However, in female-to-male (FTM) transgender individuals, natal males with birth defects, and/or severe trauma cases (or other situations), these features of the proximal corpora may not be present in the same manner, and, there may be difficulties with anchoring these devices to the pelvis.

SUMMARY

According to an aspect, an implantable device for penile construction includes a penile implant having a distal portion and a proximal portion. The distal portion includes a shaft portion configured to be disposed in a neophallus. The proximal portion defines a first strut and a second strut, and the proximal portion is configured to be attached to a pelvis structure (e.g., crus (e.g., non-boney structure of the pelvis)).

According to an aspect, an implantable device for penile construction includes a penile implant having a proximal end portion and a distal end portion. The penile implant includes an erectile body defining one or more fluid chambers and an artificial urethra, and the artificial urethra extends from the proximal end portion to the distal end portion.

According to an aspect, a method of implanting a penile implant includes coupling a penile implant to a pelvic region of a patient, the penile implant having an artificial urethra, and coupling a portion of the artificial urethra to a urethra of the patient.

BRIEF DESCRIPTION OF THE DRAWINGS

FIG. 3 illustrates an anchoring portion of a penile implant according to an aspect.

FIG. 4 illustrates an elongated member of a penile implant according to an aspect.

FIG. 5 illustrates an anchoring portion of a penile implant according to an aspect.

FIG. 11A illustrates a penile implant having an artificial urethra according to another aspect.

FIG. 11B illustrate a cross-section of the penile implant according to an aspect.

FIG. 12 illustrates a cross-section of a penile implant having an artificial urethra according to another aspect.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
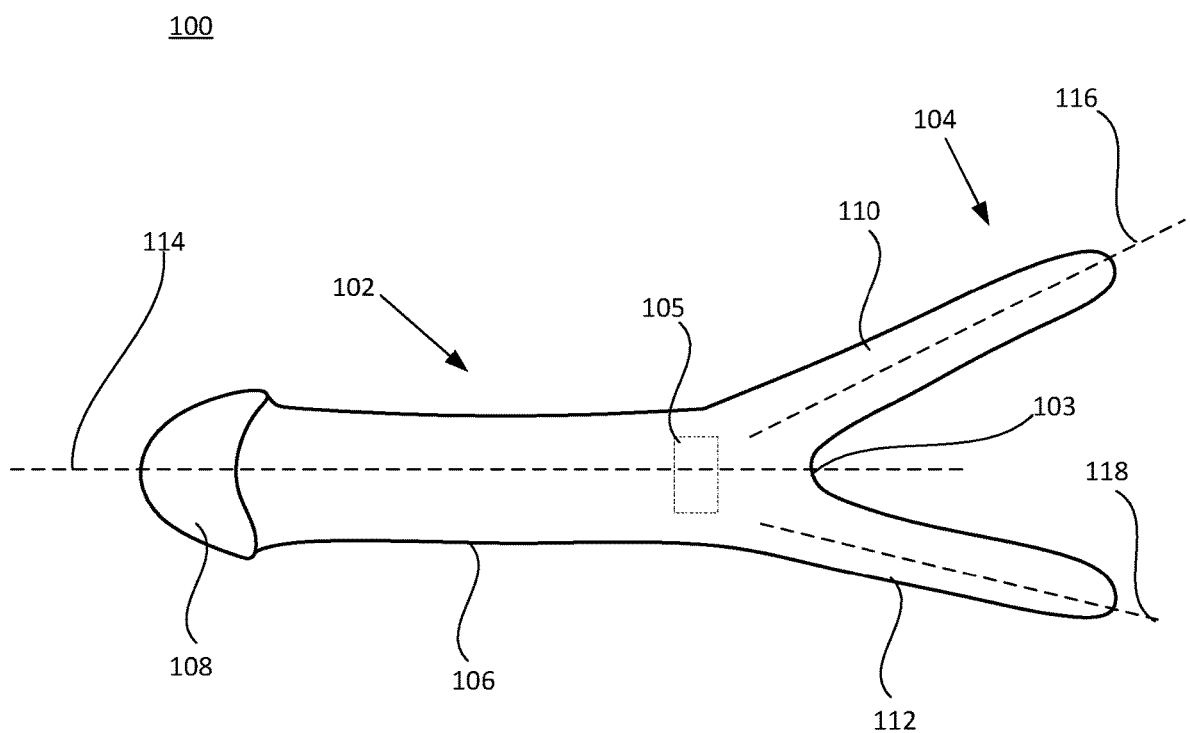
FIG. 1 illustrates a penile implant with a proximal portion that attaches to a pelvis structure according to an aspect.
Figure 2:
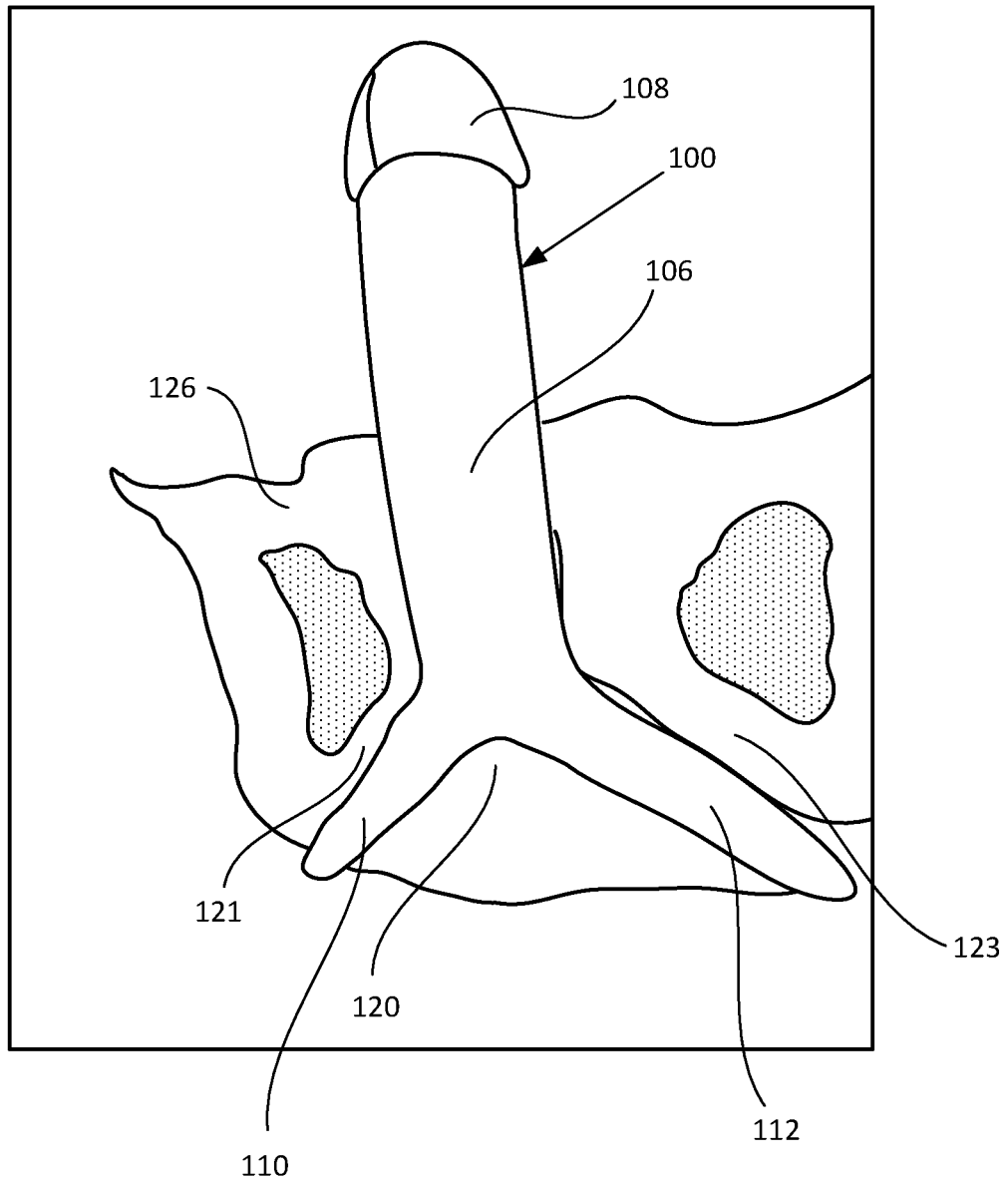
FIG. 2 illustrates the penile implant coupled to the pelvis structure according to an aspect.

FIG. 1 illustrates a penile implant 100 for a neophallus according to an aspect. FIG. 2 illustrates the penile implant 100 coupled to a pelvis structure 126 of a patient. In some examples, the pelvis structure 126 includes a crus of the pelvis. The penile implant 100 includes a distal portion 102 and a proximal portion 104. In some examples, the distal portion 102 and the proximal portion 104 form a single unitary (e.g., continuous) body. In some examples, the proximal portion 104 is a body separate from but coupled to the distal portion 102. The distal portion 102 may be a singular cylindrical body that is configured to be inserted into a cavity of the neophallus. The distal portion 102 includes a shaft portion 106 and a distal head portion 108. The proximal portion 104 is configured to be inserted into the patient's crus or attached to the pubic arch. The penile implant 100 includes an elastomeric prosthesis that provides the bulk and fills the space of the neophallus implant or it may be part of a hydraulic or mechanical system to provide transition from the flaccid to erect states.

The proximal portion 104 includes a first strut 110 and a second strut 112. The crus are different sizes and angles between the male and female pelvis. The orientation and size of the first strut 110 and the second strut 112 may vary for a male and female pelvis. The first strut 110 is disposed at a non-zero angle with respect to the second strut 112. For instance, a longitudinal axis 116 of the first strut 110 is disposed at a non-zero angle with respect to a longitudinal axis 118 of the second strut 112. The angle between the longitudinal axis 116 and the longitudinal axis 118 may be dependent on whether the pelvis is considered male or female. The angle may be greater for a female pelvis than a male pelvis. The longitudinal axis 116 may be disposed at a non-zero angle (e.g., an acute angle) (also referred to as a first angle) with respect to a central axis 114 of the distal portion 102. The longitudinal axis 118 may be disposed at a non-zero angle (e.g., an acute angle) (also referred to as a second angle) with respect to the central axis 114. In some examples, the first angle is the same as the second angle. In some examples, the first angle is different than the second angle.

Referring to FIG. 2, a portion 103 (e.g., the split) of the proximal portion 104 is configured to be positioned at a base 120 of the pelvis structure 126. The first strut 110 may be coupled to a portion 121 of the pelvis structure 126. In some examples, the first strut 110 is coupled to the portion 121 of the pelvis structure 126 using one or more sutures, wires, elongated mesh members, bone epoxy, and bone adhesive. The second strut 112 may be coupled to a portion 123 of the pelvis structure 126. In some examples, the first strut 112 is coupled to the portion 123 of the pelvis structure 126 using one or more sutures, wires, elongated mesh members, bone epoxy, and/or bone adhesive.

The takeoff angle of the distal portion 102 with respect to the first and second struts 110, 112 may be pre-set for the male or female pelvis or the takeoff angle may be adjustable to allow for variations in placement and patient anatomy. For example, the distal portion 102 may be disposed within a first plane, and portions of the first and second struts 110, 112 may be disposed within a second plane. The angle between the first plane and the second plane may define the take-off angle.

In some examples, the shaft portion 106 may define a reinforcement area 105. The reinforcement area 105 may be sutured to the pubis to mimic the suspensory ligament or the clitoral body to provide additional support. The reinforcement area 105 may have a suture pre-attached or include a mesh or other material designed for suturing into or allowing for tissue in growth.

In some examples, the penile implant 100 provides reliable support scaffold for the distal portion 102. In some examples, the penile implant 100 may reduce or prevent migration of the device during the healing process. In some examples, the penile implant 100 may provide a more secure attachment to the boney structures of the pelvis. In some examples, the penile implant 100 may mimic physiologic anchoring of native structures (e.g., uses natural tissue to anchor device). In some examples, the structure of the penile implant 100 may dampen the stress transfer during use. In some examples, the penile implant 100 may avoid the use of bone screws/penetration, which may reduce the risk of infection from the incorporation of implants into the bone. In some examples, the penile implant 100 may reduce the invasiveness of revision surgeries due to a detachable penile prosthesis and the placement in the crus. In some examples, the penile implant 100 may reduce surgical time to place the anchoring mechanism.

FIGS. 3 through 7 illustrate penile implants according to various embodiments. For example, the penile implants of FIGS. 3 through 7 illustrate an attachable anchoring mechanism (e.g., a proximal portion) that couples to a main body (e.g., a distal portion). The penile implants of FIGS. 3 through 7 may include any of the features described with reference to the previous figures.

FIG. 3 illustrates a proximal portion 304 for a female pelvis. The proximal portion 304 includes a joining portion 330 defining an attachment interface 332. The attachment interface 332 is configured to define one or more engaging features that are configured to attach to or mate with corresponding features on the distal portion (e.g., snap-fit, tongue and groove, ball and socket, etc.). In some examples, the joining portion 330 is configured to be coupled to the distal portion using one or more fastening members or material (e.g., adhesive, sutures, mesh, etc.). The proximal portion 304 includes a first strut 310 extending from the joining portion 330, and a second strut 312 extending from the joining portion 330. The second strut 312 is disposed at a non-zero angle with respect to the first strut 310.

Figure 6:
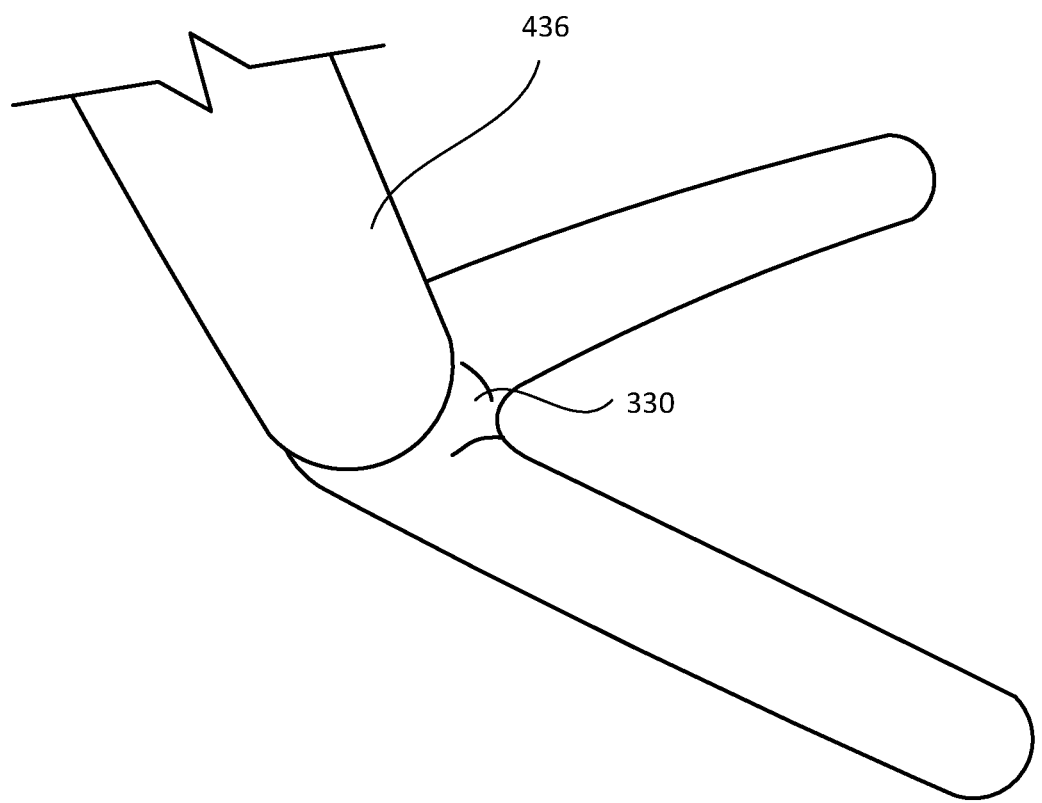
FIG. 6 illustrates a shaft of the penile implant being coupled to an anchoring portion according to an aspect.

FIG. 4 illustrates a distal portion 402 having a shaft 406 that includes a distal end portion 434 and a proximal end portion 436. FIG. 6 illustrates the proximal end portion 436 of the shaft 406 being coupled to the joining portion 330. As shown in FIGS. 4 and 6, the proximal end portion 436 is configured to be coupled to the joining portion 330 via the attachment interface 332.

Figure 7:
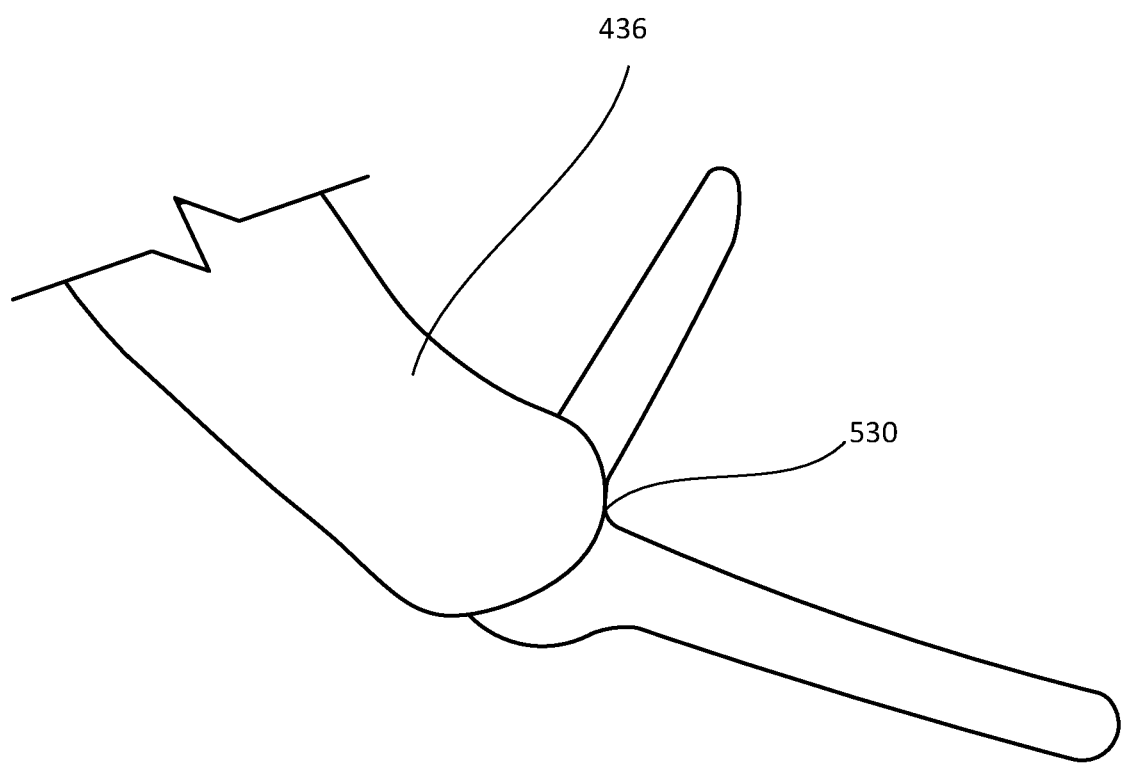
FIG. 7 illustrates a shaft of the penile implant being coupled to an anchoring portion according to an aspect.

FIG. 5 illustrates a proximal portion 504 for a male pelvis. The proximal portion 504 may be similar to the proximal portion 304 of FIG. 3. For example, the proximal portion 504 includes a joining portion 530 defining an attachment interface 532. FIG. 7 illustrates the proximal end portion 436 of the shaft 406 being coupled to the joining portion 530. As shown in FIGS. 5 and 7, the proximal end portion 436 of FIG. 4 is configured to be coupled to the joining portion 530 via the attachment interface 532. The proximal portion 504 includes a first strut 510 extending from the joining portion 530, and a second strut 512 extending from the joining portion 530. The second strut is disposed at a non-zero angle with respect to the first strut 510. However, in the example of FIG. 5, the angle between the first strut 510 and the second strut 512 is smaller than the angle between the first strut 310 of FIG. 3 and the second strut 312 of FIG. 3.

In some examples, the creation of a penis involves the creation of a tube within a tube. The inside tube is the urethra, e.g., the structure through which men urinate. The outside tube is the penile shaft. This structure, known as the neophallus is surgically attached to the pelvis. The urethra of the neophallus is connected to the existing urethra. The blood vessels and nerves are attached to those of the pelvis. The exterior of the neophallus is then sculpted to resemble a penis shaft and head.

In some examples, a majority of the neophallus complications and revision surgeries are due to infection or issues with the neourethra. These can occur anytime from days to months or years after the initial procedure are performed such as urethral stricture. A urethral stricture is the narrowing of the urethra and restricts the flow of urine from the bladder which can cause inflammation or infection. In some cases, urethral stricture develops into a complete blockage and may lead to urinary retention. Another issue that presents itself long term is due to the hair growth within the neourethra. Although the patient may have laser hair removal prior to the procedure, hair follicles with the dermis still remain or may regrow within the neourethra lumen after healing. This can lead to increased risk of infections and pain as well as numerous troublesome long-term complications such as formation of stones, diverticula, and hairballs requiring surgical intervention.

The embodiments discussed herein provide a penile implant with an artificial urethra that is configured to connect to an actual urethra of the patient. In some examples, the penile implant includes an erectile section (e.g., one or more fluid chambers). The penile implant discussed herein may provide a natural appearance and be a fully encompassed device. The penile implant discussed herein may minimize urethral complications from neophallus surgery such as hair growth, infections, and may reduce urethral strictures, as well as eliminate or reduce need for harvesting tissue for the urethra, reduce number of procedures required, reduce wait time to receive implant (e.g., minimize revisions for urethra repair), and/or increased rigidity with the multi-lumen structure, which may mimics natal male corpora anatomy.

Figure 8:
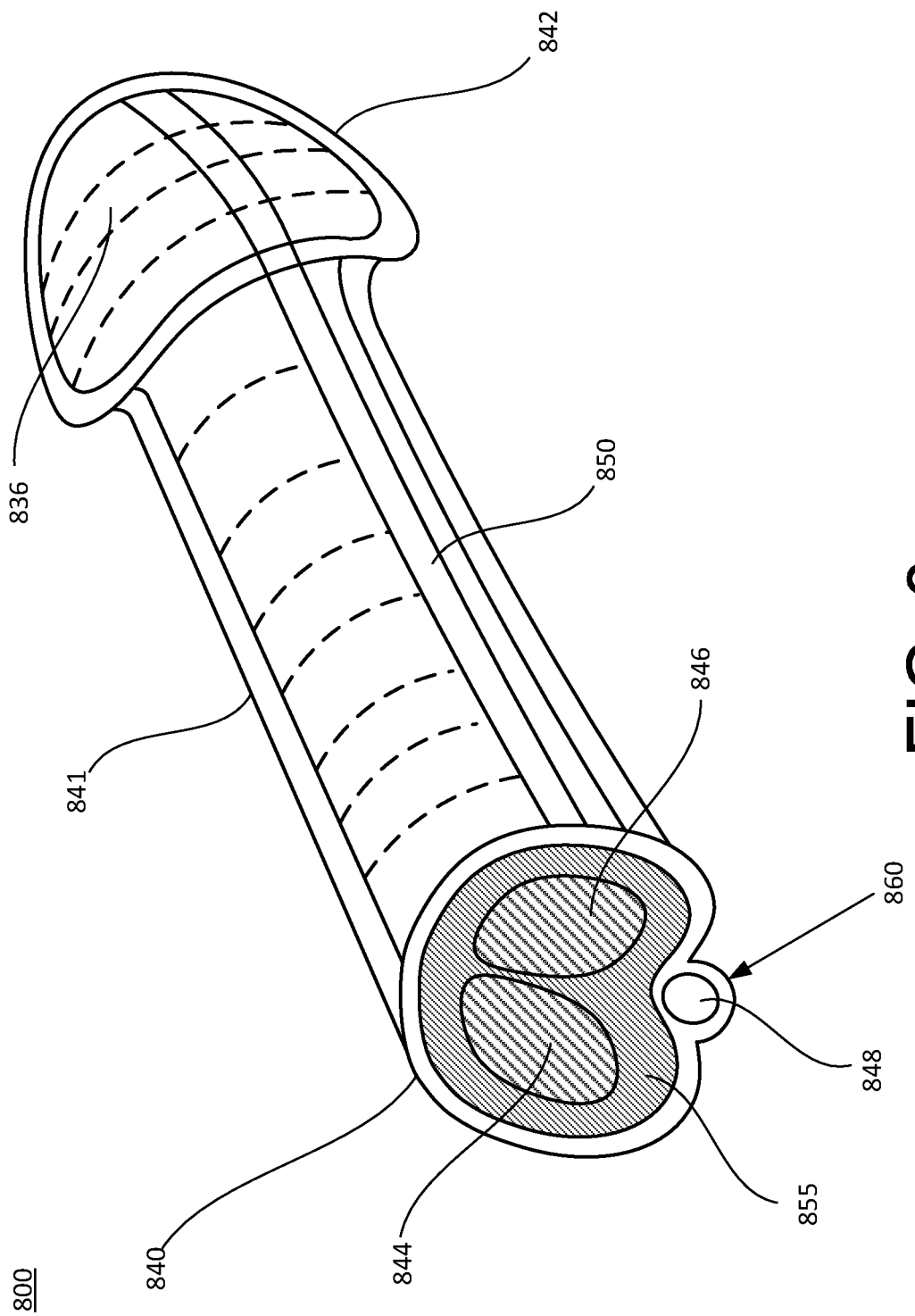
FIG. 8 illustrates a penile implant having an artificial urethra according to an aspect.

FIG. 8 illustrates a penile implant 800 having an artificial (synthetic) urethra 860 that connects to an actual urethra of a patient according to an aspect. The penile implant 800 may be used for female to male (FTM) or natal males undergoing penile construction (or reconstruction). The penile implant 800 includes a proximal end portion 840 and a distal end portion 842.

The penile implant 800 includes an erectile body 855, and a surface layer 841 encapsulating the erectile body 855. The erectile body 855 includes a glans portion 836 (e.g., an enlarged portion) at the distal end portion 842. In some examples, the erectile body 855 includes an elastomer implant body (e.g., a low durometer reinforced implant body). In some examples, the erectile body 855 includes an inflatable erectile body. In some examples, the erectile body 855 includes a malleable erectile body. In some examples, the erectile body 855 includes a multi-lumen section that may be expandable with a hydraulic pump. In some examples, the erectile body 855 includes reinforcement mesh or wires (or both or other materials) to provide increased rigidity. In some examples, the erectile body 855 includes existing cylinders placed in a pseudo-corpora shell. In some examples, the erectile body 855 includes an inner malleable core and an outer core that may be a fluid-filled, expandable section. In some examples, the glans portion 836 (e.g., the front tip) may be expandable to increase length and girth.

As shown in FIG. 8, the penile implant 800 defines a first fluid chamber 844, a second fluid chamber 846, and the artificial urethra 860. The first fluid chamber 844 and the second fluid chamber 846 may be used for girth/length expansion. The first fluid chamber 844 may be a first internal cavity that extends from the proximal end portion 840 to the glans portion 836. The second fluid chamber 846 may be a second internal cavity that extends from the proximal end portion 840 to the glans portion 836. The first fluid chamber 844 and the second fluid chamber 846 may extend parallel to each other. The portions of the first fluid chamber 844 and the second fluid chamber 846 in the glans portion 836 may provide for girth/distal tip expansion.

The artificial urethra 860 may have a urethral pathway 850 that extends between a urethral opening 848 on the proximal end portion 840 and a urethral opening 848 through the glans portion 836 on the distal end portion 842. In some examples, the urethral pathway 850 may include a surface texture to reduce or prevent bacteria growth (e.g., shark skin). In some examples, the urethral pathway 850 is formed from one or more materials that could encourage or discourage tissue ingrowth. In some examples, the urethral pathway 850 is flexible. In some examples, the length of the urethral pathway 850 is adjustable or customizable to accommodate anatomy.

The artificial urethra 860 is configured to connect to the patient's urethra. In some examples, a portion of the patient's urethra is coupled to the artificial urethra 860 at the proximal end portion 840 of the penile implant 800. In some examples, a coupling member is used to keep the artificial urethra 860 connected to the patient's urethra. In some examples, the coupling member includes a hose barb inserted into urethra lumen to prevent pull-out. In some examples, the artificial urethra 860 may include an ingrowth material to promote tissue ingrowth into the material of the artificial urethra. In some examples, the ingrowth material may include textile, ePTFE, biologic scaffold, and/or stent. In some examples, the ingrowth material is disposed along an entire length of the urethral pathway 850 or at the connection point to the patient's urethra. In some examples, the artificial urethra 860 includes an end portion (e.g., a stent-like end) that can expand and hold open the urethra opening/connection point and anchor in the artificial urethra 860. In some examples, the artificial urethra 860 may have small barbs/hooks or be suture-able for anastomosis with the patient's urethra.

Figure 9:
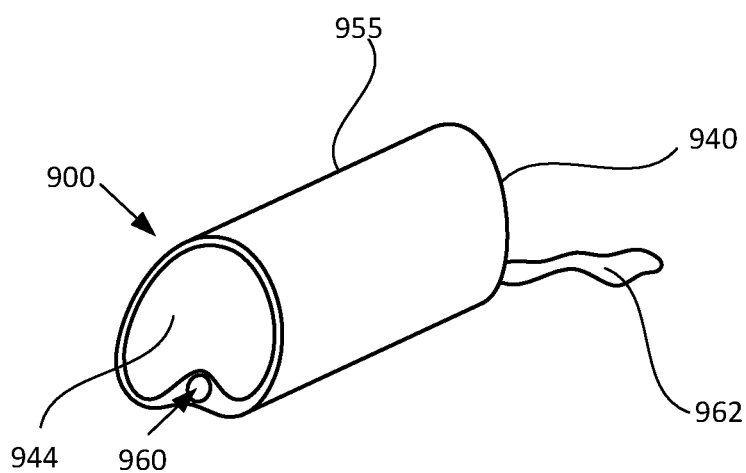
FIG. 9 illustrates a penile implant having an artificial urethra according to an aspect.

FIG. 9 illustrates a cross-sectional view of a penile implant 900 according to aspect. The penile implant 900 may include any of the features discussed with reference to the previous figures. The penile implant 900 includes an erectile body 955 defining a chamber 944 and an artificial urethra 960. In some examples, the erectile body 955 includes a silicone material. The artificial urethra 960 includes a flexible tube 962 that extends from a proximal end portion 940 of the penile implant. The flexible tube 962 may expand longitudinally to increase its length. The flexible tube 962 is configured to be coupled to the patient's urethra.

Figure 10:
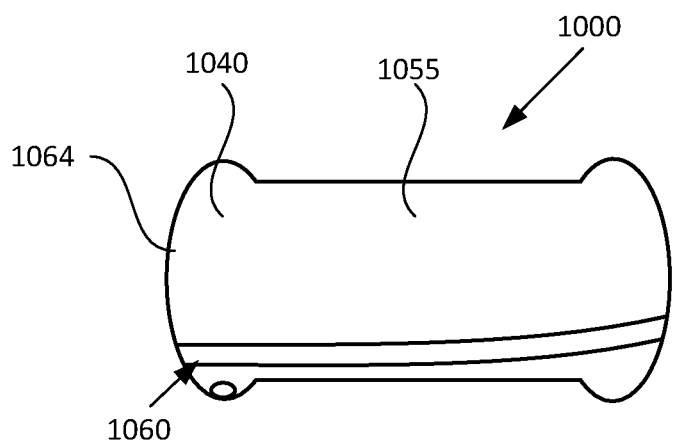
FIG. 10 illustrates a penile implant having an artificial urethra according to another aspect.

FIG. 10 illustrates a penile implant 1000 according to an aspect. The penile implant 1000 may include any of the features discussed with reference to the previous figures. The penile implant 1000 includes an erectile body 1055 defining an artificial urethra 1060. The penile implant 1000 includes a mount plate 1064 on a proximal end portion 1040 of the penile implant 1000. The mount plate 1064 is configured to attach to a pelvis of the patient.

FIG. 11A illustrates a penile implant 1100 according to an aspect. FIG. 11B illustrates a cross-section of the penile implant 1100 according to an aspect. The penile implant 1100 may include any of the features discussed with reference to the previous figures. The penile implant 1100 includes an erectile body 1155 that defines a fluid chamber 1144 and an artificial urethra 1160. The penile implant 1100 includes a proximal end portion 1140 and a distal end portion 1142. The proximal end portion 1140 includes a rear-tip extender 1141. In some examples, the erectile body 1155 includes an inner core 1170 and an outer core 1172. In some examples, the inner core 1170 includes the artificial urethra 1160. In some examples, the outer core 1172 includes the fluid chamber 1144. The artificial urethra 1160 includes a flexible tube 1162 that extends from the erectile body 1155 at the proximal end portion 1140. The flexible tube 1162 is configured to be coupled to the patient's urethra. The penile implant 1100 includes a transfer tube 1166 fluidly connected to the fluid chamber 1144 and a pump assembly 1168. The pump assembly 1168 is configured to transfer fluid to and from the fluid chamber 1144.

FIG. 12 illustrates a cross-section of a penile implant 1200 according to an aspect. The penile implant 1200 may include any of the features discussed with reference to the previous figures. The penile implant 1200 may be a full-functional pendulous synthetic body. The penile implant 1200 includes an erectile body 1255 that includes a first cylinder 1274 and a second cylinder 1276. The erectile body 1255 includes an artificial urethra 1260. The penile implant 1200 includes an overmold portion 1275 disposed on portions of the erectile body 1255. In some examples, the overmold portion 1275 includes a silicone material. In some examples, the overmold portion 1275 includes a low durometer silicone material. In some example, the overmold portion 1275 is configured to capture or stimulate in growth. The penile implant 1200 includes a tissue layer 1278. In some examples, the tissue layer 1278 includes stretched or harvested (or cadaveric) tissue.

Figure 13:
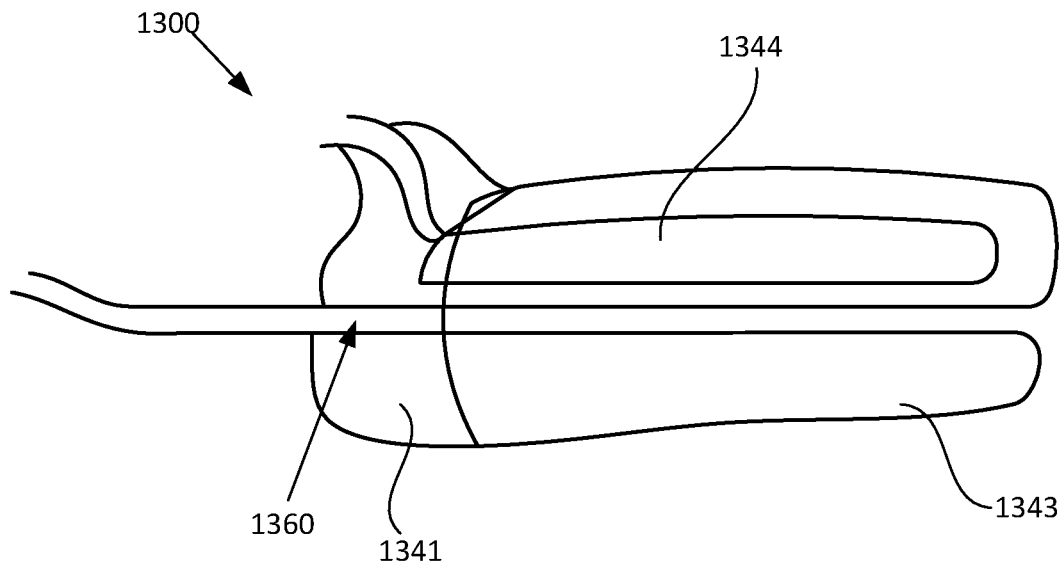
FIG. 13 illustrates a penile implant having an artificial urethra according to another aspect.

FIG. 13 illustrates a penile implant 1300 according to an aspect. The penile implant 1300 may include any of the features discussed with reference to the previous figures. The penile implant 1300 includes an artificial urethral 1360, a fluid fill chamber 1344, an overmolded rear tip 1341, and an overmolded front tip 1343.

Figure 14:
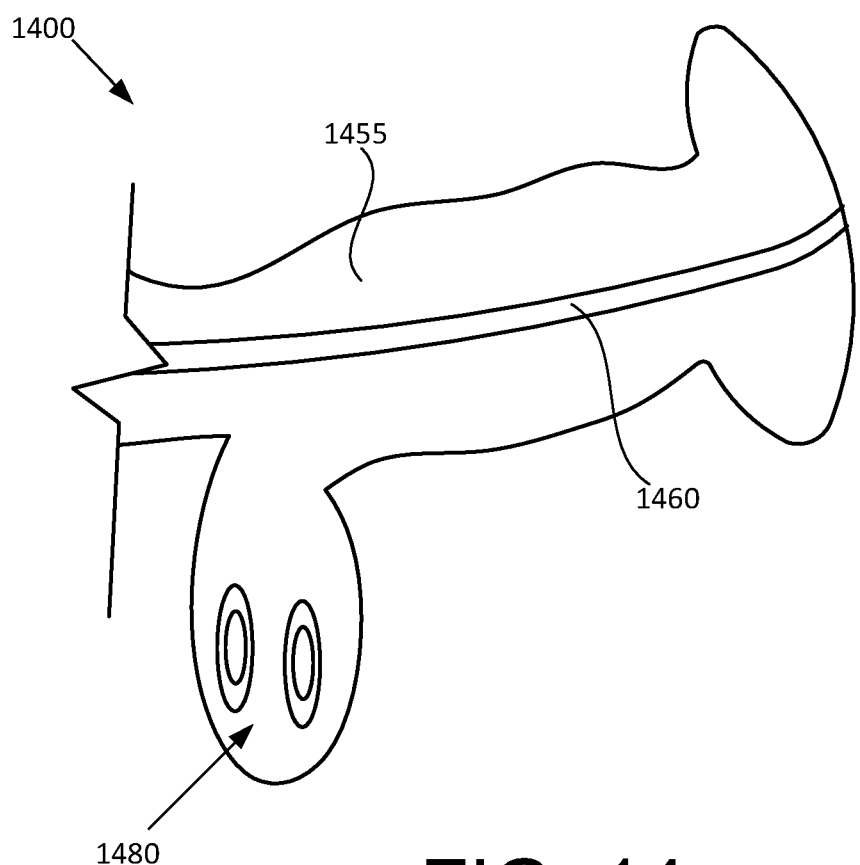
FIG. 14 illustrates a penile implant having an artificial urethra according to another aspect.

FIG. 14 illustrates a penile implant 1400 according to an aspect. The penile implant 1400 may include any of the features discussed with reference to the previous figures. The penile implant 1400 includes an erectile body 1455 having an artificial urethral 1460 and synthetic testicles 1480.

Figure 15:
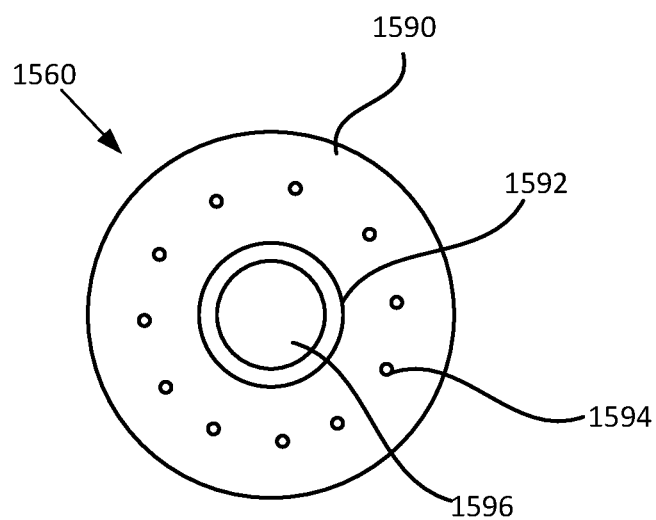
FIG. 15 illustrates a cross-section of an artificial urethra according to an aspect.

FIG. 15 illustrates a cross-section of an artificial urethral 1560 according to an aspect. The artificial urethral 1560 includes a urine passage 1596, an inner ring 1592, and an outer ring 1590. The inner ring 1592 includes a first polymer material. In some examples, the first polymer material is silicone. The outer ring 1590 includes a second polymer material. In some examples, the second polymer material is polytetrafluoroethylene. In some examples, the outer ring 1590 includes reinforcement fibers 1594.

Figure 16:
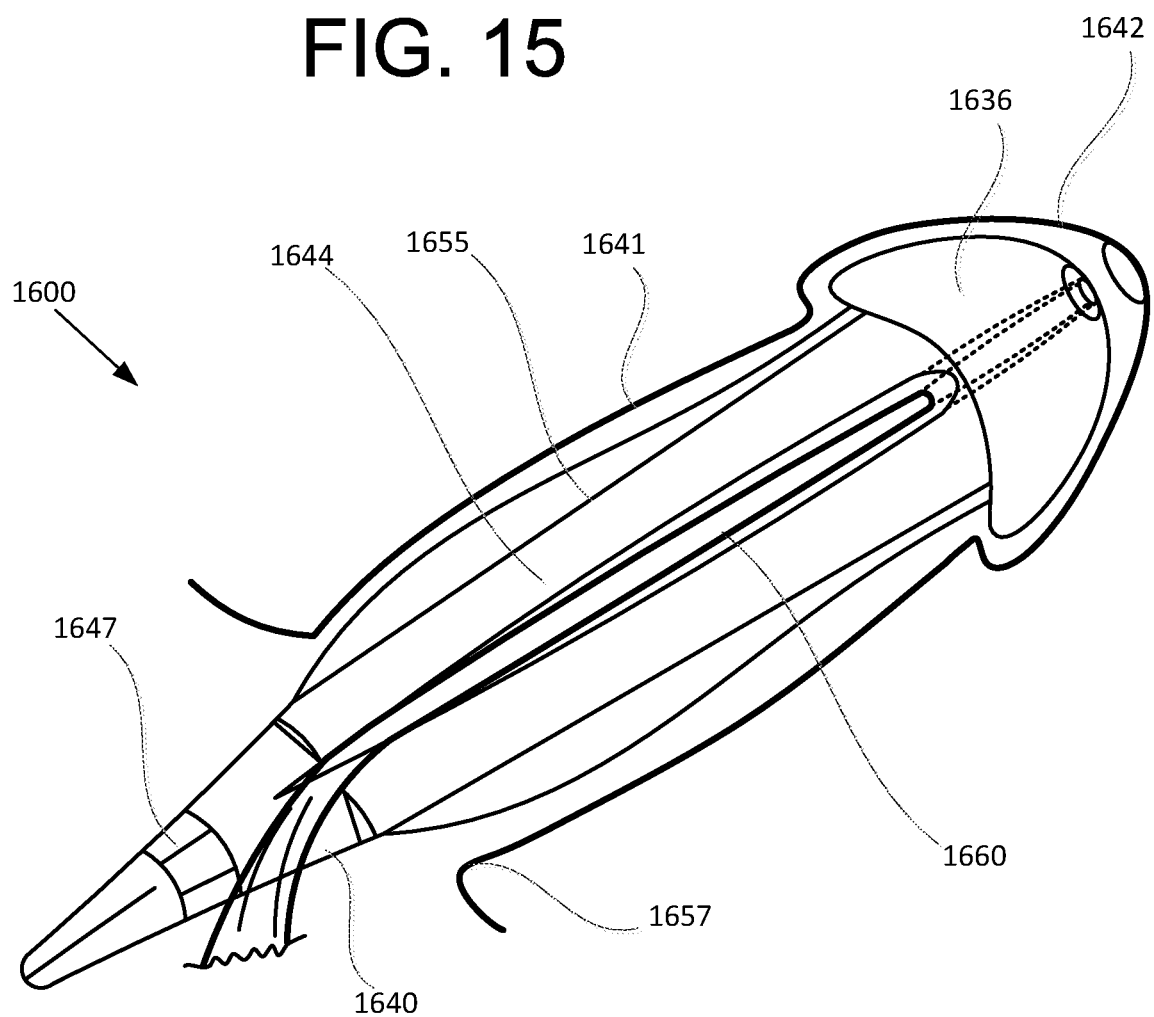
FIG. 16 illustrates a penile implant having an artificial urethra according to another aspect.

FIG. 16 illustrates a penile implant 1600 according to an aspect. The penile implant 1600 may include any of the features discussed with reference to the previous figures.

The penile implant 1600 includes a proximal end portion 1640 and a distal end portion 1642. The penile implant 1600 includes an erectile body 1655, and a surface layer 1641 encapsulating the erectile body 1655. The surface layer 1641 may define textile exterior surfacing (e.g., laminated to the surface of the erectile body 1655). The erectile body 1655 includes a glans portion 1636 (e.g., an enlarged portion) at the distal end portion 1642. The erectile body 1655 includes one or more fluid channels 1644 running through the erectile body 1655 (e.g., the entire erectile body 1655) from the proximal end portion 1640 to the glans portion 1636.

The erectile body 1655 defines an artificial urethral 1660. The artificial urethral 1660 defines a urethral pathway that extends along a caudal side of the penile implant 1600 and is used to position and establish a functional urethra through the pendulous neophallus. In some examples, the urethral pathway enters the implant at a rear tip portion 1647, along the shaft, through the glans portion 1636, and exits through the distal tip. In some examples, the rear tip portion 1647 defines a hydraulic access point for the fluid chambers 1644. In some examples, penile implant 1600 includes one or more textile surfacing tails 1657 for suture anchoring and native tissue attachment.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. An implantable device for penile construction, the implantable device comprising:
    a penile implant having a distal portion and a proximal portion, the distal portion including a shaft portion configured to be disposed in a neophallus, the shaft portion having a reinforcement portion configured to be coupled to a suture to provide support to the penile implant, the proximal portion defining a first strut and a second strut, the proximal portion configured to be attached to a pelvis.

2. The implantable device of claim 1, wherein the second strut is disposed at a non-zero angle with respect to the first strut.

3. The implantable device of claim 1, wherein the proximal portion is a separate component from the distal portion, the proximal portion configured to be coupled to the distal portion.

4. The implantable device of claim 1, wherein the proximal portion defines an attachment interface configured to attach to a proximal end portion of the distal portion.

5. The implantable device of claim 1, wherein the first strut is configured to be positioned proximate a first portion of the pelvis while the second strut is configured to be disposed proximate a second portion of the pelvis.

6. An implantable device for penile construction, the implantable device comprising:
    a penile implant having a distal portion and a proximal portion, the distal portion including a shaft portion configured to be disposed in a neophallus, the shaft portion having a reinforcement portion including a mesh portion configured to be coupled to a suture to provide support to the penile implant, the proximal portion defining a first strut and a second strut, the proximal portion configured to be attached to a pelvis.

7. The implantable device of claim 6, wherein the second strut is disposed at a non-zero angle with respect to the first strut.

8. The implantable device of claim 6, wherein the proximal portion is a separate component from the distal portion, the proximal portion configured to be coupled to the distal portion.

9. The implantable device of claim 6, wherein the proximal portion defines an attachment interface configured to attach to a proximal end portion of the distal portion.

10. The implantable device of claim 6, wherein the first strut is configured to be positioned proximate a first portion of the pelvis while the second strut is configured to be disposed proximate a second portion of the pelvis.

11. An implantable device for penile construction, the implantable device comprising:
a unitarily formed penile implant having a distal portion and a proximal portion, the distal portion including a shaft portion, the proximal portion having a first strut and a second strut, the proximal portion configured to be attached to a pelvis wherein the shaft portion includes a reinforcement portion configured to be coupled to a suture to provide support to the penile implant.

12. The implantable device of claim 11, wherein the second strut is disposed at a non-zero angle with respect to the first strut.

13. The implantable device of claim 11, wherein the first strut is configured to be positioned proximate a first portion of the pelvis while the second strut is configured to be disposed proximate a second portion of the pelvis.

14. The implantable device of claim 11, wherein the shaft portion includes the reinforcement portion having a mesh portion and being configured to provide support to the penile implant.

\* \* \* \* \*